United States Patent [19]

Cushman et al.

[11] 4,251,730
[45] Feb. 17, 1981

[54] PANORAMIC DENTAL X-RAY MACHINE X-MOTION DRIVE

[75] Inventors: Robert H. Cushman, Princeton, N.J.; Anthony Ciavattoni, Staten Island, N.Y.; John J. Flynn, Hazlet, N.J.; Thomas J. Schubert, Staten Island, N.Y.

[73] Assignee: Pennwalt Corporation, Philadelphia, Pa.

[21] Appl. No.: 25,706

[22] Filed: Apr. 2, 1979

Related U.S. Application Data

[63] Continuation-in-part of Ser. No. 2,148, Jan. 9, 1979, abandoned.

[51] Int. Cl.³ ............................................. A61B 6/14
[52] U.S. Cl. .............................................. 250/439 P
[58] Field of Search .......... 250/439 P, 439 R, 445 R, 250/449

[56] References Cited

U.S. PATENT DOCUMENTS 4,125,774  11/1978  Ciavattoni et al. ............. 250/439 P Primary Examiner—Davis L. Willis
Assistant Examiner—T. N. Grigsby

[57] ABSTRACT

Panoramic dental X-ray machine possessing mechanical and electronic simplicity for providing both continuous and discontinuous radiographs of a dental arch area. The machine includes an excursion mechanism which causes a tubehead-camera assembly to uninterruptedly circularly orbit the patient's head at a constant speed. A drive mechanism is employed which controls the shifting or transport of the patient along an X-axis only, when either continuous or discontinuous images are desired. The kVp and milliamperes remain constant during the entire exposure of the patient to the X-rays as well as the rotational speed of the tubehead-camera assembly, and no attenuating members are required in the X-ray path for varying intensity of the X-ray beam.

12 Claims, 17 Drawing Figures

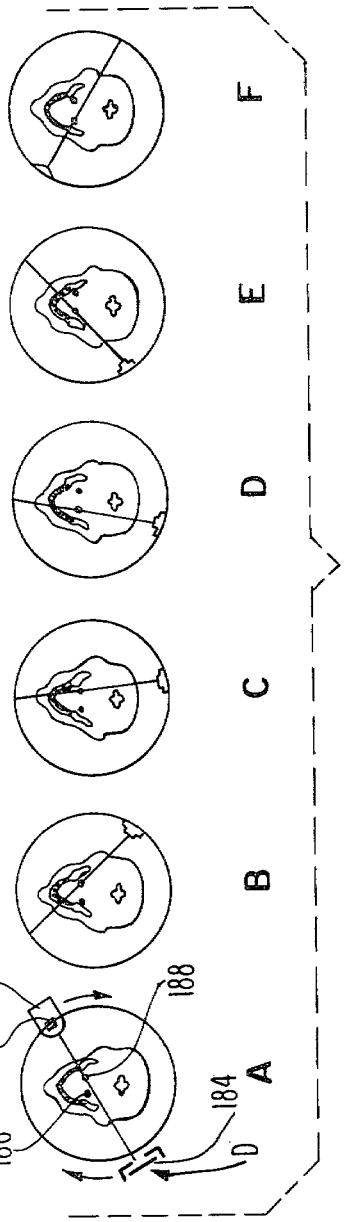

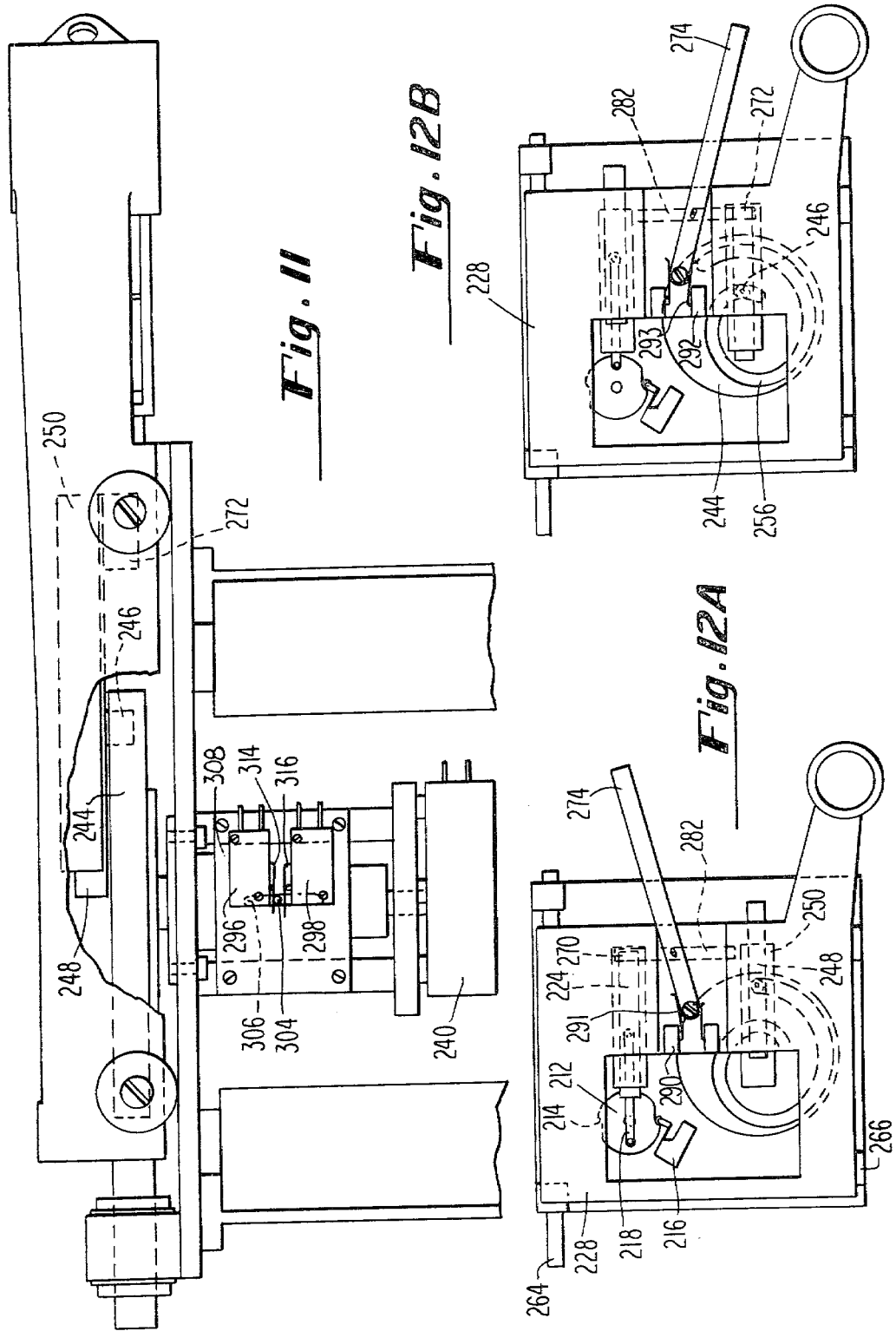

PANORAMIC DENTAL X-RAY MACHINE X-MOTION DRIVE

STATEMENT OF THE INVENTION

This application is a continuation-in-part of our co-pending application, Ser. No. 002,148, filed Jan. 9, 1979, for "Panoramic Dental X-Ray Machine X-Motion Drive", assigned to the assignee hereof and now abandoned.

The present invention relates to X-ray apparatus and more particularly concerns X-motion chair shift mechanisms for providing both continuous and discontinuous panoramic radiographs of dental arch areas.

BACKGROUND OF THE INVENTION

Prior art panoramic dental X-ray apparatus are well known in the art. Some provide a continuous image of the dental arch area and commonly employ an X-ray source and X-ray film supported on a rotatable carrying arm which orbits a patient situated in the beam path. The dental arch however is not usually circular or elliptical, but represents a complex curve. Mechanisms have been devised which permit the X-ray source and X-ray film to travel about the patient along a curve which closely parallels the complex shape of an ideal dental arch, thus insuring substantially proper focus to each tooth being radiographed.

In addition to insuring proper depth of focus for each tooth, it is essential that the speed of X-ray film travel be adjusted in accordance with the more arcuate shape of the incisors-cuspid area, or anterior region, as compared to the molar-biscuspid area, or posterior region, if proper spacing and distances occupied by each tooth is to be portrayed on the continuous radiograph. Mechanisms for controlling film travel speed; orbiting the X-ray source and X-ray film about the patient; and shifting the chair in accordance with a predetermined pattern; must be painstakingly integrated if meaningful continuous radiographs are to be provided. Such radiographs provide the dentist with a panoramic view of the teeth and associated structures and are useful diagnostic aids in many phases of dental practice.

Various other prior art apparatus provide a discontinuous, or split image panoramic radiograph which possesses certain advantages. Here, the dentist is provided with additional interpretive information since two distinctly different views of the centrals area are provided. For example, consider the split image radiograph as two separate films. A pathology located on the left half is noted with respect to its relationship to the centrals, or incisors. The same pathology is located on the right half. If the image of the pathology, such as an impacted canine, appears to move away from the patient's midline, the pathology is palatally located. Conversely, if the image of the pathology moves toward the midline, it is labially located. Additionally, overlying spinal shadows which would be cast over the central-biscuspid region are eliminated since X-rays are not generated when the spine is aligned with the X-ray source and film.

The present invention discloses a panoramic dental X-ray machine capable of providing either type radiographic image, i.e., continuous or discontinuous.

BRIEF DESCRIPTION OF THE DRAWINGS

FIG. 5 is a sectional view of the belt-fastening means used in the excursion mechanism.

FIG. 6 is a perspective view of the cam arrangement for providing a split image panoramic radiograph.

FIG. 7 is a diagrammatic representation depicting progressive steps in making a discontinuous panoramic radiograph.

FIG. 11 is an elevational view of the chair transport mechanism top plate assembly in its most rightward position.

FIG. 12A and 12B are plan views showing the relative positions of certain components of the chair transport mechanism after completion of discontinuous image and continuous image cycles respectively.

DETAILED DESCRIPTION OF THE INVENTION

FIGS. 1 through 7 of the drawings are substantially identical with those of U.S. Pat. No. 4,125,774, of Anthony Ciavattoni et al., assigned to the present assignee.

Figure 1:
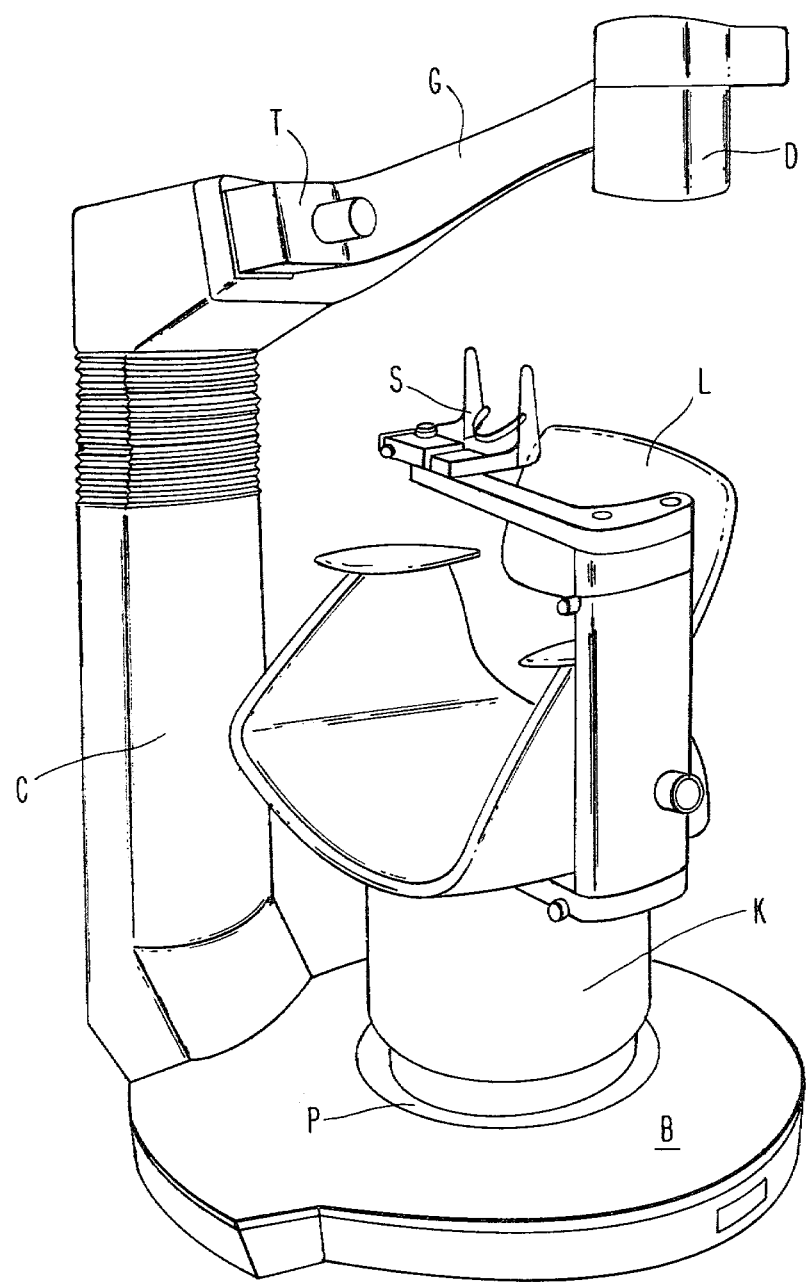
FIG. 1 is a perspective view of the panoramic dental X-ray machine of the invention.

Referring now to FIG. 1 of the drawings, the panoramic X-ray machine comprises a base B having a stationary platform P disposed generally centrally thereof. Platform P supports a patient chair L including means S for supporting the chin and head of a patient. A column C is caused to rotate around chair L, the column carrying a tubehead T, a camera supporting arm G, and a camera D which includes the usual film holding means. The chair transport mechanism is located below chair L, within shroud K, the mechanism being bolted securely to stationary platform P. The mechanism for causing column C to rotate around stationary platform P is supported and partially housed in base B, and is hereinafter referred to as the excursion mechanism.

A. Excursion Mechanism

Figure 2:
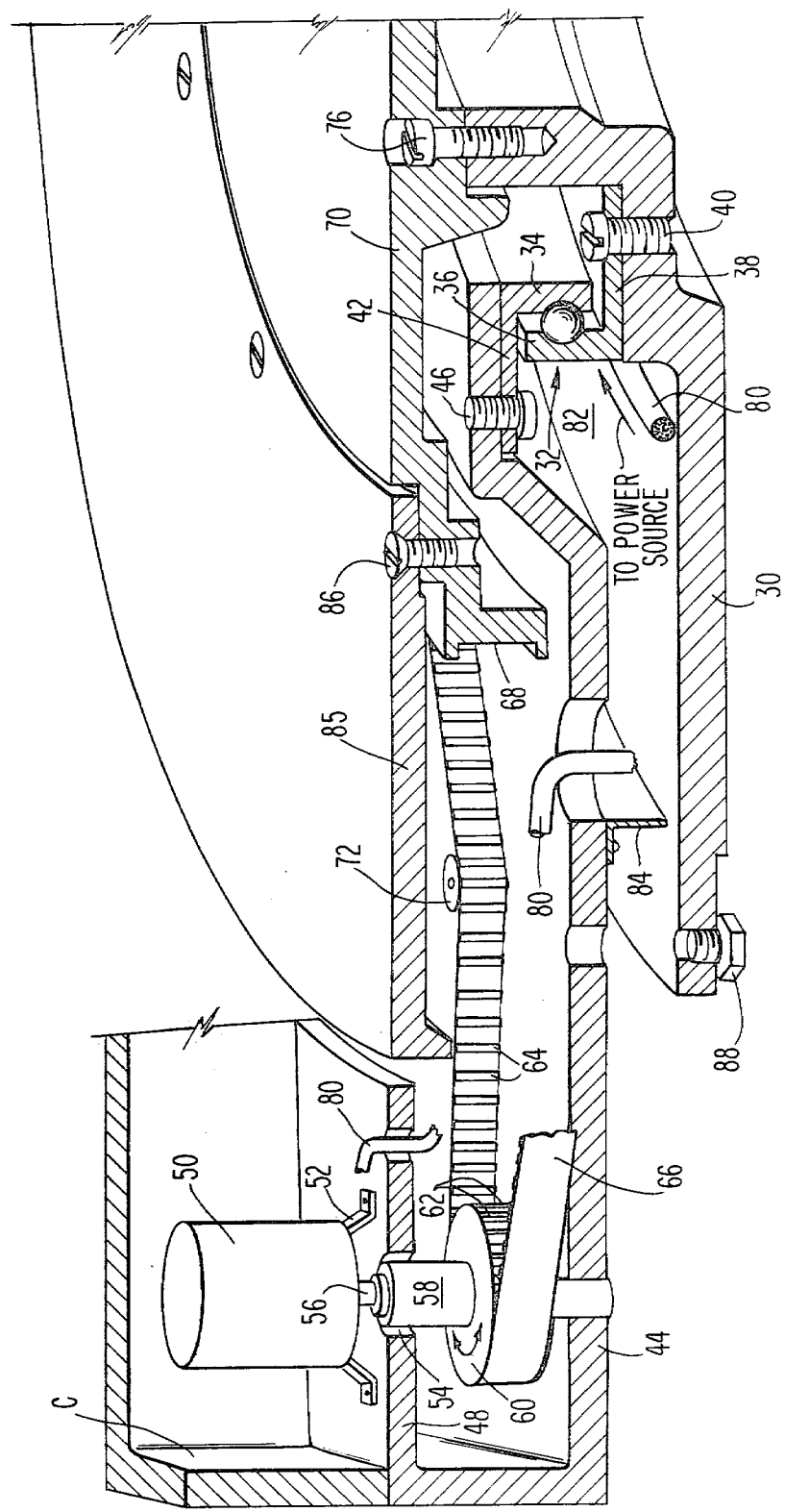
FIG. 2 is a cutaway perspective view of a portion of the base and excursion mechanism of the machine shown in FIG. 1.

In FIG. 2, a base plate 30, preferably an aluminum casting, carries a circular flange mounted bearing 32 having an inner race 34 and an outer race 36. Outer race 36 includes a lower flange 38 which is secured to base plate 30 by circumferentially spaced screws 40. Similarly, upper flange 42 of inner race 34 carries rotating disc 44. Upper flange 42 and rotating disc 44 rotate as a unit and are held together by means of circumferentially spaced shoulder screws 46.

Rotating disc 44 carries column C which is provided with a horizontal plate member 48, upon which is mounted a synchronous step motor 50 by means of brackets 52. An opening 54 is provided in horizontal plate 48 through which shaft 56 of motor 50 communicates with a conventional electromagnetic slip clutch 58. Clutch 58 serves to couple shaft 56 with sprocket 60 which is rotatably mounted to rotating disc 44. Sprocket 60 is provided with teeth 62 which coact with spaced projections 64 on a belt 66. The belt is accomodated within an annulus 68 provided around stationary platform P which supports the patient chair L.

It should be emphasized that belt 66 does not rotate around platform P. Belt 66 is held immovable against annulus 68 at that portion of the annulus farthest removed from sprocket 60 by means to be described more fully hereafter. To further clarify, any given point on belt 66, such as point E, for example, will always contact a specified point, and no other point, on annulus 68, such as point F, regardless of the direction of limited rotation of rotating disc 44. Belt 66 provides the means therefore for translating the rotation of sprocket 60 into limited orbital rotation of rotating disc 44 and column 18.

A flexible electric cable 80 passes up through column C for connecting the power source to the X-ray source and camera, and to the motor (not shown) which elevates or lowers the tubehead assembly in column C. The cable is also connected to motor 50, slip clutch 58, and a limit switch assembly to be described hereinafter. In order to insure unimpeded vertical movement of the tubehead assembly and the orbiting of column C, cable 80 will be provided with a sufficient length. To that end, a space 82 is provided above base plate 30 to permit coiling and uncoiling of cable 80 during movement of the tubehead and column. A cable control band 84 is mounted to an underside portion of rotating disc 44 for restricting cable 80 within space 82.

A removable cover plate or step plate 85, suitably an aluminum casting, protects the excursion mechanism as well as affording means upon which the patient may step and rest his feet. Step plate 85 is removably attached to stationary platform P by screws 86. Leveling screws 88 are provided in base plate 30.

Figure 3:
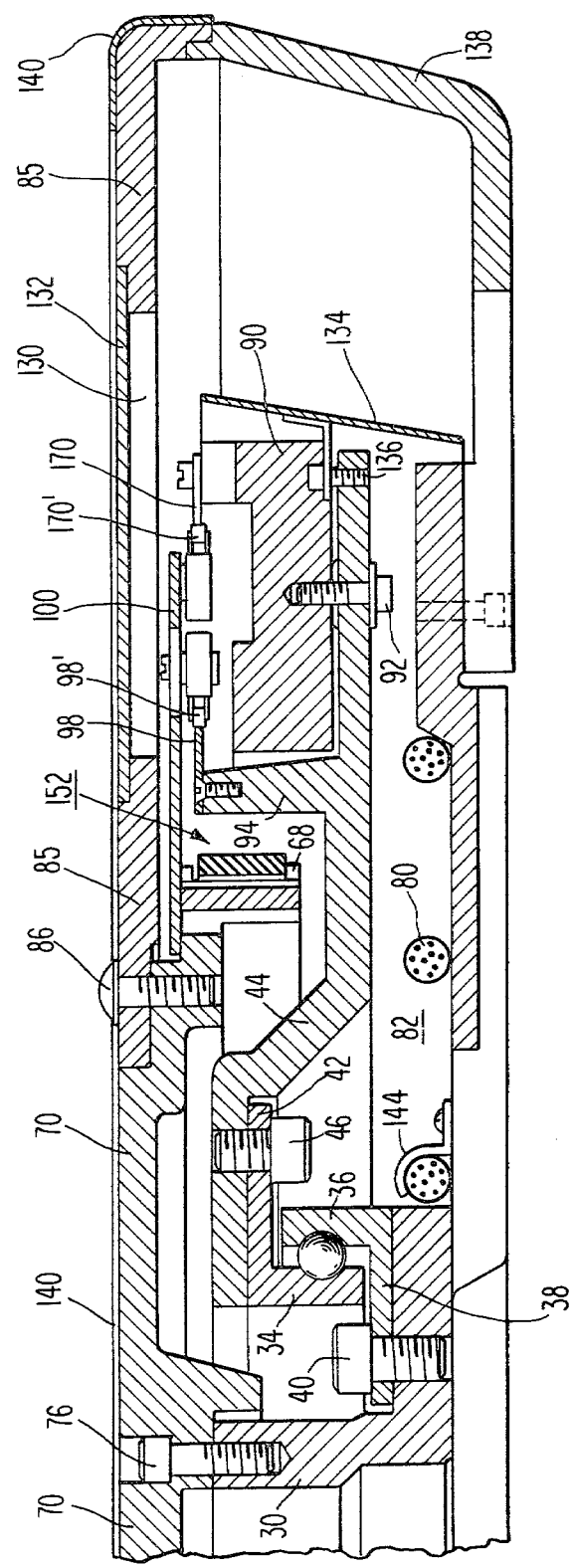
FIG. 3 is a sectional view of another portion of the base and excursion mechanism.
Figure 4:
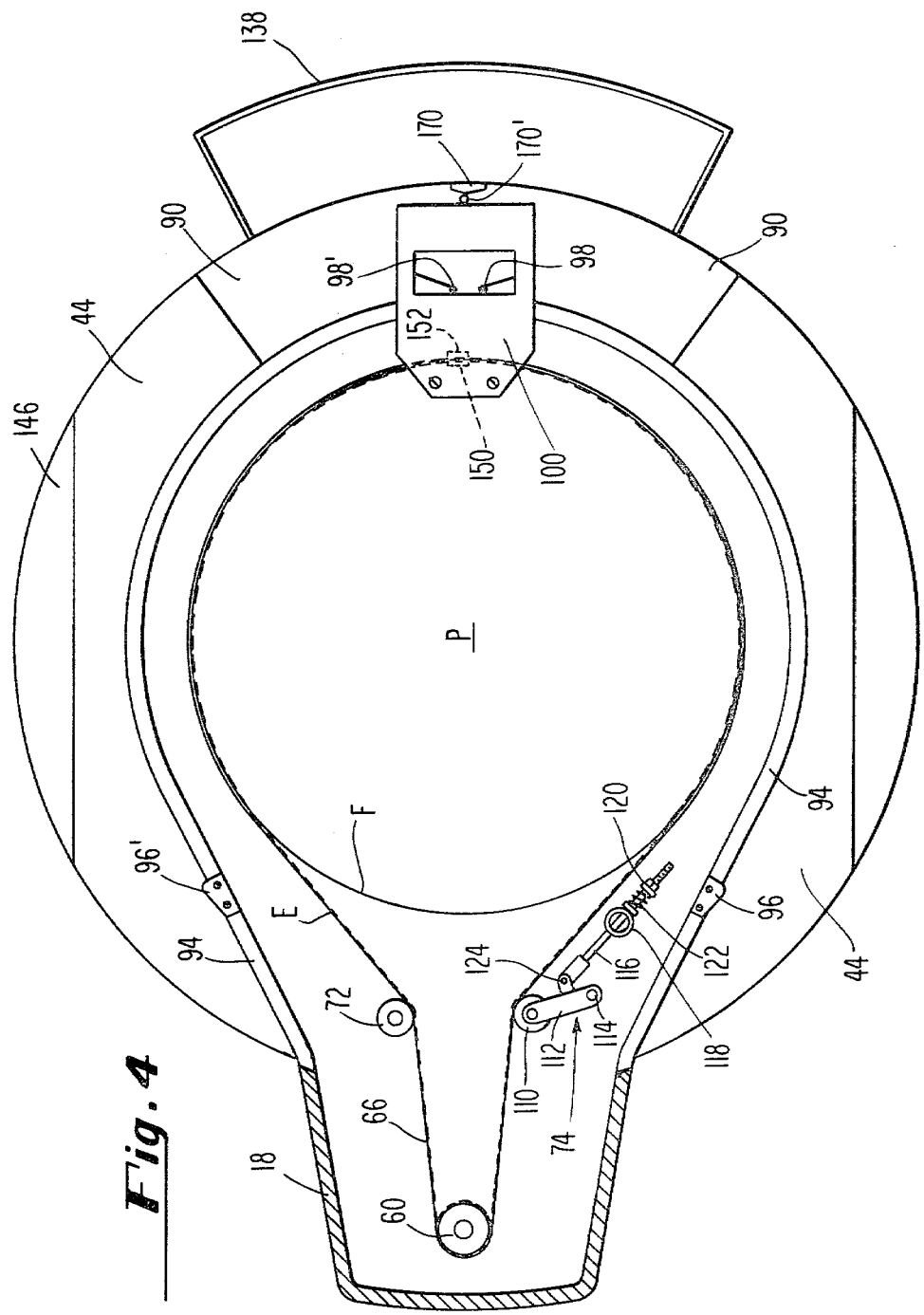
FIG. 4 is a plan view, partially in section, of the excursion mechanism with portions removed for clarity.

For a better understanding of the excursion mechanism, reference should now be made to FIGS. 3 and 4 wherein a balancing weight 90, suitably cast iron, is shown seated on an outer portion of rotating disc 44, the weight 90 being positioned in counterbalancing relation to column C. Screws 92 maintain balance weight 90 in a fixed position on rotating disc 44. An annular ring 94 upstands from rotating disc 44 and carries a pair of cams 96 and 96' which respectively actuate limit switches 98 and 98' to limit the total excursion of rotating disc 44 to about 240°. Limit switches 98 and 98' are carried on a switch plate 100 mounted on stationary platform P. More specifically, when rotating disc 44 moves in a counterclockwise direction, switch 98 will be actuated by cam 96 to open the circuit to motor 50. Conversely, cam 96' actuates limit switch 98' when rotating disc 44 moves in a clockwise direction to open the circuit to motor 50. Cams 96 and 96' are so positioned that column C and rotating disc 44 are permitted only about 240° of rotation in either direction. Circuitry for the cam-microswitch arrangement is conventional and are not detailed herein.

Adjustable idler pulley assembly 74 comprises an idler wheel 110 rotatable on arm 112 which is pivotally mounted to rotating disc 44 by screw 114. A holder 116 is slidably insertable through a nut 118 which is fixedly secured to rotating disc 44. Thus, idler wheel 110 will be displaced inwardly to increase tension on belt 66 when screw 120 is tightened against compression spring 122 to cause arm 112 to pivot clockwise on screw 114 by means of pivot pin 124.

Step plate 85 is provided with a recess 130 for receiving a removable access plate 132 for easy access to switch plate 100.

A skirt 134 extends around rotating disc 44 and is mounted thereto by screws 136 while a step plate support member 138 is bolted to base plate 30. A step plate cover 140, preferably rubber or vinyl, is fitted over the step plate.

A clamp 144 may be employed to secure cable 80 against base plate 30.

Rotating disc 44 may be provided with removable wings 146 to enable passage of the X-ray machine through restricted openings.

Annulus 68 of stationary platform P has a cut-out area, or notched recess 150 for receiving a belt-fastening assembly 152 therewithin (FIG. 5) comprising an outer plate 154 and an inner plate 156 which includes grooves 158 for accepting projections 64 of belt 66. The plates 154 and 156 are secured together by screws 160.

In the operation of the excursion mechanism, any rotary motion of shaft 56 of motor 50 will not be coupled to sprocket 60 until sufficient voltage is supplied to the coils of clutch 58. That is, the clutch will be permitted to "slip" until actuated. However, once actuated by a sufficient voltage, rotation of sprocket 60 will be effected. Since belt 66 is held fast against annulus 68 in the vicinity where belt-fastening assembly 152 engages notched recess 150 provided in stationary platform P, rotation of the sprocket causes column C and rotating disc 44 to orbit around the stationary patient platform. Thus, belt 66 will translate the rotational movement of sprocket 60 into a clockwise or counterclockwise excursion of the column depending upon the direction of rotation of the sprocket. More specifically, rotation of sprocket 60 in a clockwise direction causes column C and rotating disc 44 to orbit in an opposite direction, and vice-versa.

Reversing the direction of rotation of motor 50, and circuitry supplying the necessary voltage to actuate slip clutch 58 is well known. For the purposes of this invention, step motor 50 is geared down by conventional means to permit 1.83 rpm of the column and rotating disc.

B. Discontinuous Image Radiographs

Since the present invention contemplates an X-motion drive chair mechanism, features well known in the art for operating a panoramic dental X-ray machine are not described herein. For example, it is well known that as column C is rotated about a patient, means must be provided to accomplish an independent movement of the X-ray film in order to achieve proper exposure of the film. The movement must be in a particular time sequence with respect to the rotation of column C and movement of the patient chair but as such mechanism forms no part of the present invention, none will be described, and the structure to accomplish this has been omitted from the drawings for the purpose of simplification. However, the cam and microswitch means for effectuating interruption of the generation of X-rays is essential for providing the discontinuous panoramic images. Thus, reference is again made to FIGS. 3 and 4, and to FIG. 6, wherein cam 170 is mounted to rotating disc 44 to actuate switch 170', adjustably mounted on switch plate 100. Switch 170' is connected to the X-ray source. As rotating disc 44 rotates counterclockwise, for example, switch 170' will ride on cam surface 170A to open the circuit to the X-ray source. In a discontinuous, or split image panoramic radiograph, X-rays are not generated when the spine is aligned with the X-ray source and X-ray film, resulting in a radiograph having a distinctive white band between the centrals. A white band approximately 1 inch wide would result if the speed of travel of the X-ray film was not substantially decreased during the entire period the X-rays were not being generated, i.e., when traversing the spine. A one inch wide band is considered objectionable by many dentists since it is not only wasteful of valuable space on the radiograph, but tends to hinder diagnosis by the dentist. For discontinuous or split panoramic images, image distortion of the centrals would result if the white band were entirely eliminated. It should be mentioned herein that discontinuous panoramic images requires the establishment of two pivot points, one each behind the left and right molar areas. Essentially, true image portrayal is thus achieved because the distance from an X-ray pivot point to any tooth to be X-rayed from that pivot point is practically constant. That is, after one-half the dental arch is X-rayed, the center of rotation to the other pivot point is effectuated by a chair shift, mechanism for which is later described in detail. In order to prevent image distortion which would result if an attempt were made to superimpose the images of the centrals, a white band of proper width, approximately ¼ inch, provides a true perspective image of the centrals as well as separate views for increasing the interpretive capabilities by the dentist.

In accordance with the above, switch 170', connected to the X-ray source as aforementioned, will be opened by cam surface 170A to stop any further generation of X-rays by the X-ray source. Upon continued counterclockwise movement of rotating disc 44, switch 170' is then actuated by cam surface 170B to close the circuit to the X-ray source to start the flow of X-rays once more. In the embodiment described, power to the X-ray source is removed for about 2 seconds.

To further clarify, assume rotating disc 44 is now rotating in a clockwise direction. Since switch 170' was last actuated by cam surface 170B which returned the switch to its normally closed position while the rotating disc was then rotating counterclockwise, switch 170' will now be opened by cam surface 170B to cut off power to the X-ray source. By adjusting the speed of travel of the X-ray film during the period in which X-rays are not being generated, the width of the white band can readily be controlled.

In further clarification of the above, reference is made to FIG. 7 wherein tubehead T includes an X-ray source 180 for activating X-ray film 184 contained within camera D. Camera D includes the usual slot for permitting passage of radiation therethrough. A pair of pivot points 186 and 188 are selected behind the left and right molar areas respectively which serve as imaginary axes for rotating the tubehead-camera assembly.

In diagrams A, B, and C, pivot point 188 is used as the axis of rotation for radiographing the left half for the dental arch area of the patient. When the tubehead-camera assembly reaches the position shown in diagram C, the patient chair is shifted to the right by the X-motion drive chair mechanism, later described, in order that the axis of rotation of the tubehead-camera assembly coincides with pivot point 86 (diagram D) for radiographing the right half dental arch area.

It should be emphasized that orbiting of the tubehead-camera assembly about the patient is not interrupted while the chair is shifting (between diagrams C and D) but that power to the X-ray source is shut off as previously described. The circuit to the motor in the X-motion drive chair shift mechanism to thereby shift the chair may conveniently be initiated when X-ray generation is cut off by means of cam 170 and switch 170'. Circuitry between the motor and switch 170' is conventional and is not described or shown in the drawings.

Diagrams C and D reveal that two distinctly different views of the centrals, or incisors, is provided by the discontinuous, or split image panoramic radiograph made in accordance with the above. The images are sharply focused and possess a "forgiving" focal trough, i.e., one which readily accommodates a variety of dental arch sizes and asymmetry.

The tubehead-camera may be rotated in a counterclockwise direction in which case the chair will be shifted to the right. Circuitry is conventional and is not shown.

Figure 8:
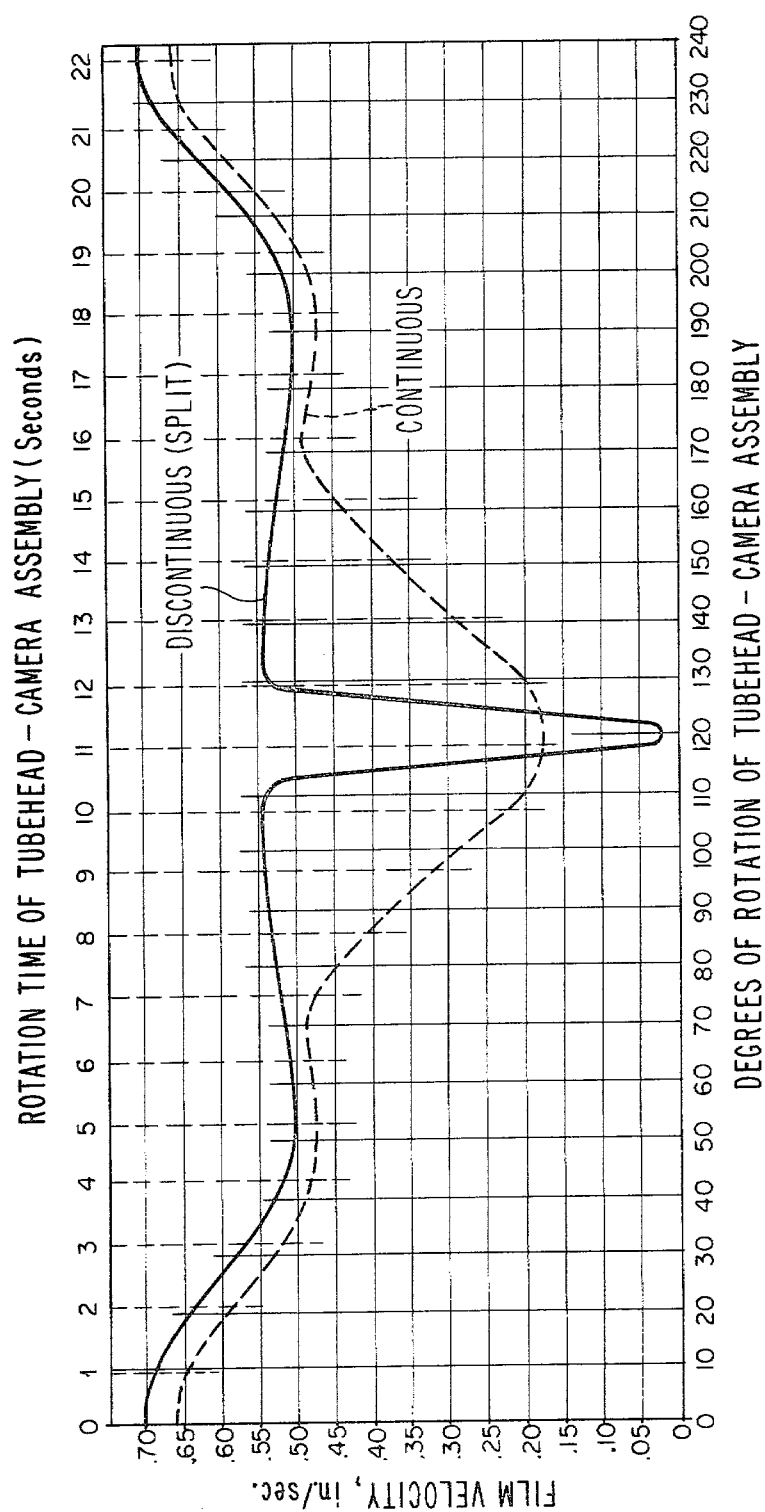
FIG. 8 is a graphic representation of film travel speed plotted against degrees of rotation of the tubehead-camera assembly and time consumed for such rotation in obtaining continuous and discontinuous image radiographs.

The film drive may be started simultaneously with the start of rotation of the tubehead-camera assembly by a single switch. The structure of the film drive, including means for selecting either mode of operation, i.e., continuous or discontinuous, including means to decrease film travel speed when the patient's spine is being X-rayed, forms no part of the present invention. In order to better understand the nature and operation of the invention, reference will be made to FIG. 8, wherein film travel speed for discontinuous images decreases from about 0.70 to about 0.55 inches per second in about 10 seconds of excursion of the tubehead-camera. Within the next 1⅔ seconds or so, the film travel speed uniformly decelerates to about 0.025 inches per second and then uniformly accelerates back to about 0.55 inches per second before tracing a mirror image curve to 0.70 inches per second, the entire excursion consuming about 22 seconds.

The chair shift occurs between about 110° to 130° of excursion of the tubehead-camera assembly which coincides with the alignment of the spinal column with the X-ray source and camera.

C. Continuous Image Radiographs

In the continuous mode of operation, the patient is seated in the patient chair and the tubehead-camera assembly positioned to start X-raying the left or right molar area. As with the discontinuous mode, the film drive mechanism may be started simultaneously with the rotation of the tubehead-camera assembly by a single switch. Referring again to FIG. 8, the speed of travel of the film is graphically illustrated therein. The patient's chair however moves only a portion of the time the film is moving within the camera or when the tubehead-camera assembly is rotating. That is, the chair remains substantially motionless for about the initial and final 6½ seconds of film travel and tubehead-camera rotation.

Figure 16:
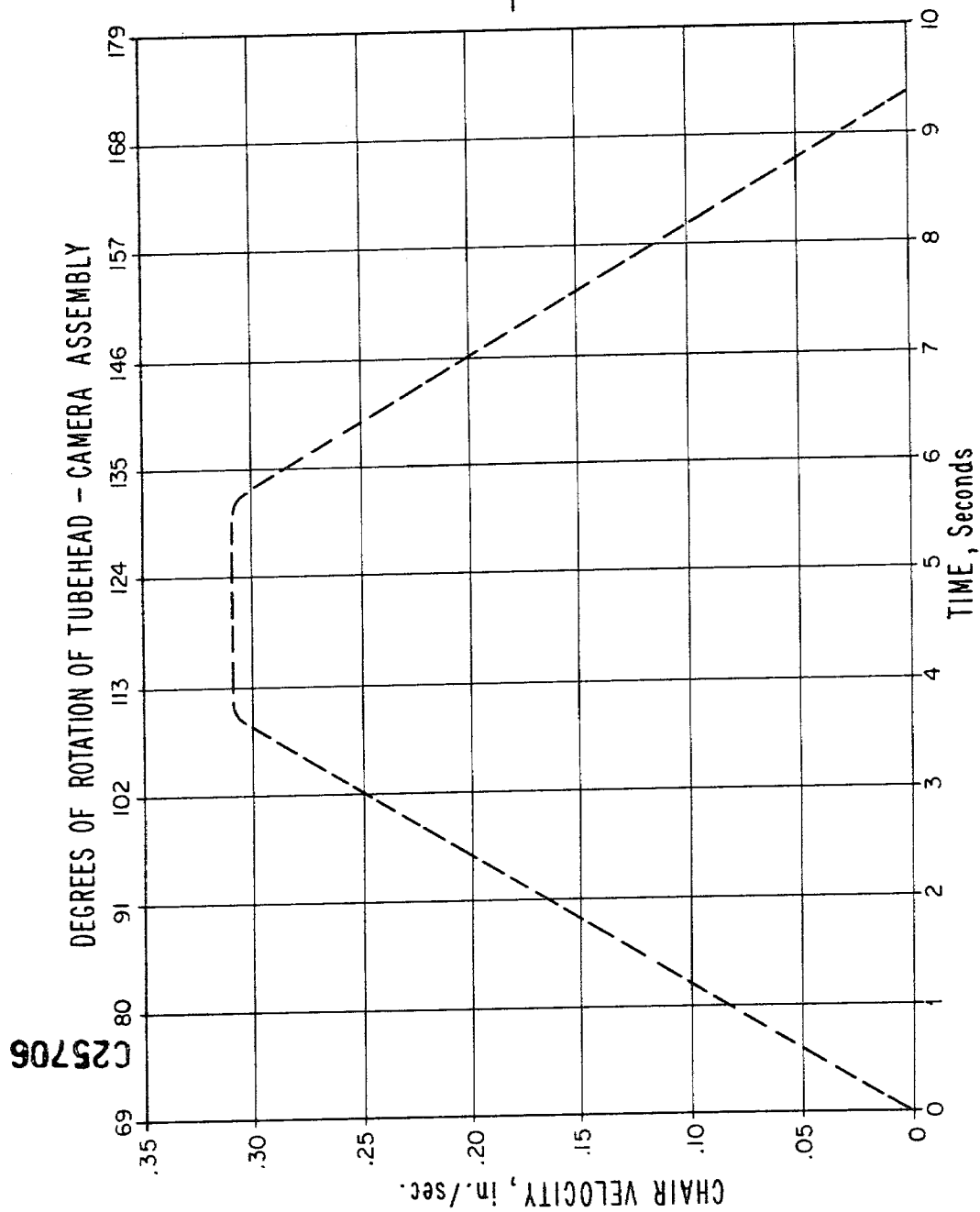
FIG. 16 is a graphic representation of chair velocity in the continuous mode of operation plotted against degrees of rotation of the tubehead-camera assembly (rounded off to nearest degree) and time consumed therefor.

Additionally, the patient's chair does not move at a constant speed. Referring to FIG. 16, the chair starts its movement through X-motion chair transport mechanism at about the start of the X-raying of the biscuspids, or about ˜0° after the tubehead starts its rotation, or when the film speed starts to decelerate more rapidly. For the next 3¾ seconds, or until about 110° of tubehead-camera assembly rotation, the speed of the chair accelerates at a constant rate, and then plateaus at a constant speed for about 1¾ seconds or until the tubehead has traveled about 129° at which time the chair uniformly decelerates for approximately 3¾ seconds, or until the tubehead's excursion has completed about 170° of rotation.

Fortuitously, the present straight line or X-motion chair shift, as opposed to or compared with prior art X-Y or non-straight line chair movement, provides the ideal relationship where the X-ray film is moving at its slowest speed past the slot in the camera during that time when the X-rays are passing through the patient's dense spinal column. It should be appreciated that the speed at which the film is caused to move past the slot in the camera is dictated by the relationships involving the rotational speed of the tubehead-camera assembly around the patient; the chair shift speed; and the desired focal trough location, which, in turn, is dictated by the arcuate shape of the dental arch of the patient.

Parenthetically, when the more complex prior art X-Y chair motion is employed, speed of the film moving past the camera slot when the central region was being X-rayed was required to be much faster in order to retain the same focal trough shape. It is apparent therefore that the present X-motion chair shift permits increased radiation to be received by the film per unit of film length when X-raying the centrals, thus compensating for the increased object density and resultant loss of radiation in penetrating the dense spinal column in the mid-portion of the radiograph.

The X-motion chair shift, in turn, makes it possible to retain the kVp, mA, and tubehead-camera rotational speed constant during the entire exposure of the patient to the X-rays in the continuous mode of operation, including the period when the X-rays are penetrating the spinal column of the patient in the central region. Thus, any need to incorporate attentuating members in the path of the X-rays and to remove the members when X-raying the spinal column and then to replace the removed attenuating members is now obviated. Similarly, the X-motion chair shift eliminates the need alternatively to increase either or both the kVp and mA or decrease the rotational speed of the tubehead-camera when the X-rays are passing through the spinal column. Both the insertion, removal and re-insertion of an attenuating member, and varying the intensity of the X-rays or the rotational speed of the tubehead-camera are alternative techniques used in the prior art to provide a substantially constant average density continuous radiograph when the X-ray beams are penetrating the spinal column.

The aforementioned plateauing of the chair speed, i.e., a constant maximum chair speed of approximately 0.31 inches/second for about 1¾ seconds while X-raying the centrals has been found to substantially reduce or minimize "overlap", which may be defined as the obscuring or masking of diagnostic information on interproximal caries. The reduction of overlap is accomplished by maintaining the X-ray central beam axis as close as possible to perpindicular to the tangent to the dental arch. An additional and very important advantage to be derived from the present X-motion chair shift and "plateauing" of chair speed at the centrals resides in the achievement of a focal trough having maximum width at the centrals, where normally the focal trough thereat is very narrow.

Actuation of chair transport after about 70° of tubehead rotation, and stopping of the chair's movement after about 170° of tubehead rotation may readily be accomplished by cam-limit switch means. For example, cam means affixed to annular ring 94 could actuate limit switch means mounted on stationary platform P. Circuitry for such a cam-limit switch arrangement is conventional and is not shown in the drawings. The mechanism or structure for controlling film speed is not being claimed herein.

D. Chair Transport Mechanism

The chair transport mechanism or X-motion drive mechanism, is located below chair L, within shroud K, and is bolted securely to stationary platform P by suitable means or through a base plate (not shown). Referring now to FIGS. 9 through 14, the chair transport mechanism is provided with pedestal 202 which supports bottom plate 204. A motor 208, hereinafter referred to as the chair shift motor, is mounted beneath bottom plate 204. Chair shift motor 208 is conveniently self-braking, shaded pole, nonreversible, A.C. and may suitably have a 16 rpm output shaft 210 connected to cam disc 212. The cam disc is symmetrical, having a pair of opposed lobes 214 disposed 180° apart, which lobes contact limit switch assembly 216 to successively close and open the circuit to chair shift motor 208 each time it is actuated. For discontinuous or split image mode of operation, a chair shift consumes almost two seconds to complete its travel of approximately 1¾".

A drive rod 218 has one of its ends 220 pivotally, off-centrally connected to cam disc 212. The other end 222 of drive rod 218 is connected to a pin 223 received by an underportion of an inner race member 224 which is slidably received within an outer race member 226. Outer race 226 is securely threadedly mounted to an underside portion of a top plate 228. Outer race 226 may be provided with a ball bearing slide plate 229 (FIG. 13) to insure substantially vibration-free motion between the race members. Inner race 224, outer race 226, and slide plate 229 comprise a slide assembly.

Operation of the X-motion chair shift mechanism is later described.

Figure 13:
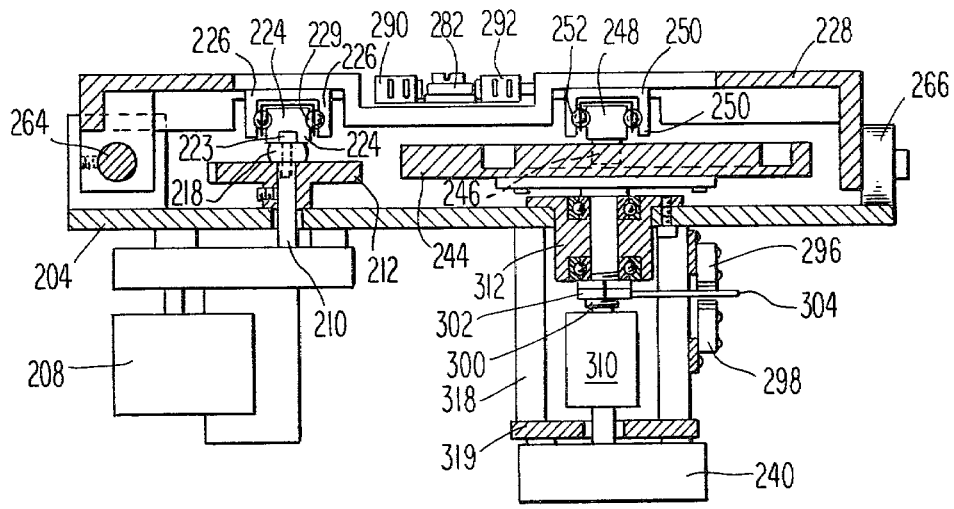
FIGS. 13 and 14 are sectional views of the chair transport mechanism of FIG. 10 taken substantially along lines 13—13 and 14—14 respectively thereof.

Mechanism for transporting chair L, suitably mounted on top plate 228, in the X-direction, or from left to right or right to left, for continuous mode of operation, comprises a reversible, synchronous motor 240, mounted beneath bottom plate 204 (FIG. 13). Motor 240 includes an output shaft, later described, which causes cam 244 to rotate therewith, suitably a plate cam, although a drum type cam could also be employed. A cam follower 246 is rigidly pinned to an underportion of another inner race member 248, which inner race 248 comprises a component of another slide assembly identical with the slide assembly abovediscussed, which slide assembly also includes an outer race 250, and ball bearing slide plate 252.

The output shaft of motor 240 rotates at a speed of about 3.66 rpm. A speed of rotation considerably slower would impose an undue load on cam 244 and motor 240 by requiring groove 256, disposed in cam 244, to contact cam follower 246 at a severe angle, or an excessively large angle.

The rate of change of distance of groove 256 from the center of rotation of cam 244 determines the speed of chair travel. Thus, the chair would remain substantially motionless if the cam follower rode in a radial groove having a center of rotation coincident with the output shaft of motor 240.

Figure 10:
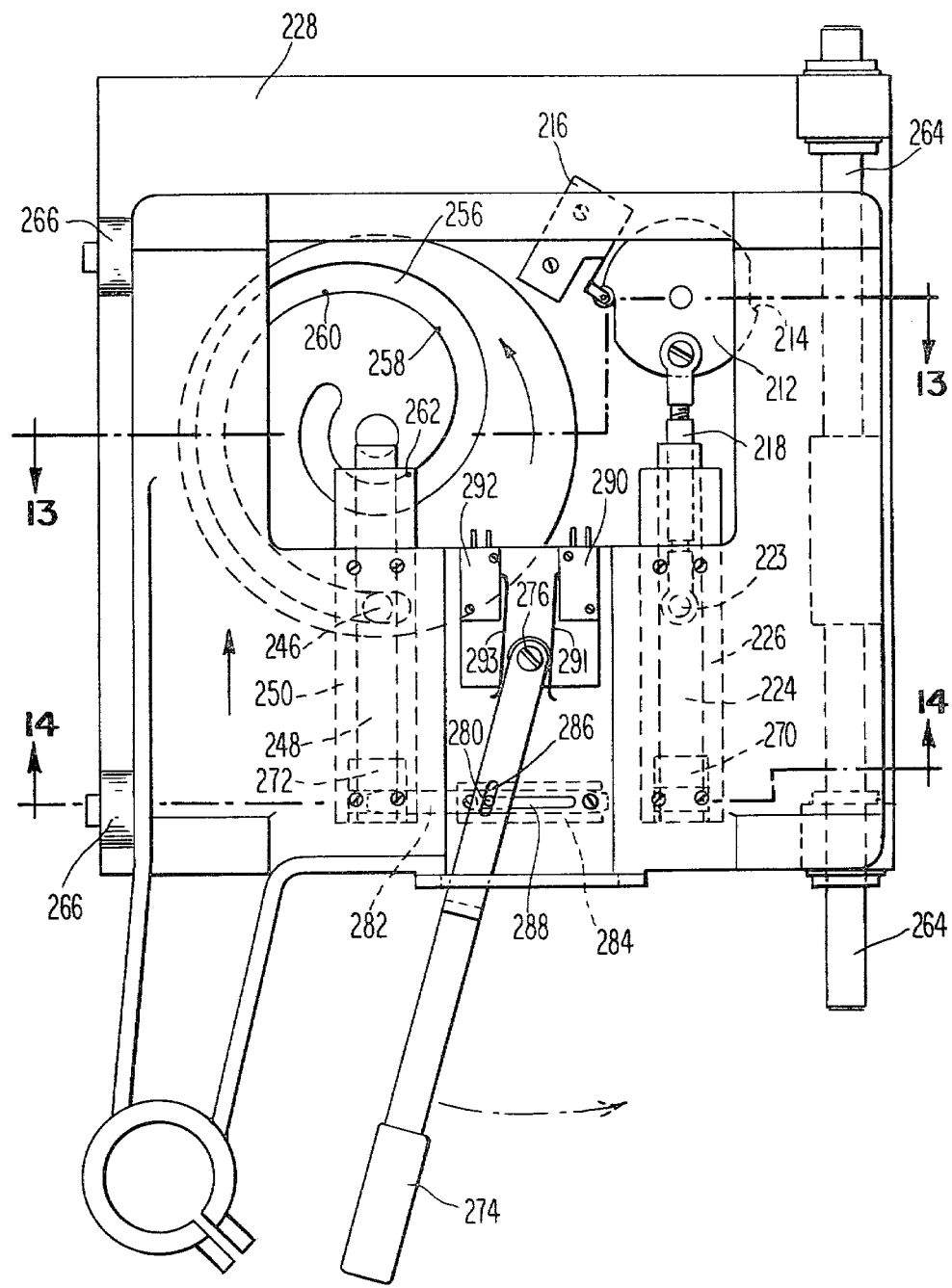
FIG. 10 is a plan view of the chair transport mechanism shown in FIG. 9 with portions of the top plate removed.

In the present invention, the patient's chair does not travel at a constant speed when the dental arch area is being X-rayed to obtain continuous images thereof. The chair travel speed is coordinated with the speed of travel of the X-ray film. As abovementioned, film travel speed is slower when the cuspid-incisor area, or anterior region, is X-rayed, as compared to the posterior regions of the mouth. In order to compensate for the arcuate shape of the anterior region, a proportional increase in chair speed is needed at that region if true image portrayal of the cuspid-incisor area is to be achieved. That is, at the midline of the incisors area where film travel speed is slowest, chair L should be moving at its fastest speed. Groove 256 is so designed to provide such nonconstant chair travel. Thus, chair L will decelerate its speed of travel at a substantially constant rate when cam follower 246 rides within groove 256 as the rate of change in distance of the groove from the center or rotation of plate cam 244 uniformly decreases. Conversely, the chair will accelerate its speed at a substantially constant rate when cam follower 246 rides within groove 256 as its rate of change in distance from the center of rotation of cam 244 uniformly increases. In FIG. 10, as plate cam 244 is rotated in a clockwise direction, chair L will be transported to the right. When the cam rotates in the other direction, chair L will travel to the left.

Point 258 indicates the approximate point where the rate of change of distance of groove 256 from the center of rotation of cam 244 is the greatest. Numberals 260 and 262 indicate generally the points at which the chair starts or terminates its constant rate of acceleration or deceleration, depending upon direction of rotation of the cam.

Top plate 228 is movable with respect to bottom plate 204 through a slide bar arrangement 264 mounted on one side of the chair transport mechanism and a pair of wheels 266 mounted on its other side, in addition to the slide assemblies aforementioned.

E. Electrical-Mechanical Safety Interlock

The chair transport mechanism is provided with cooperating electrical and mechanical safety interlock features and coordinates film travel speed with the selected mode of chair transport.

Figure 9:
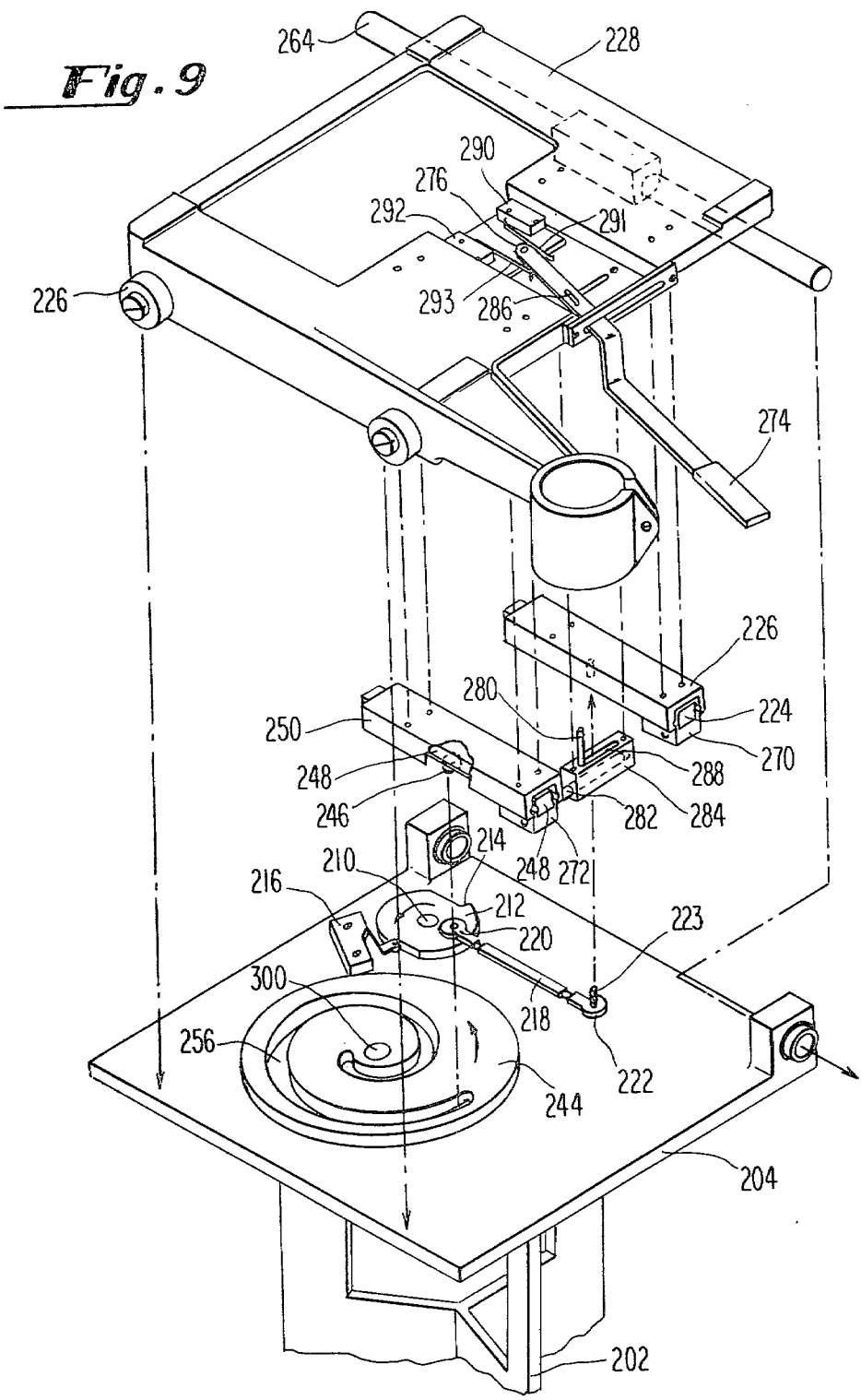
FIG. 9 is an exploded perspective view of the chair transport mechanism of the present invention.
Figure 14:
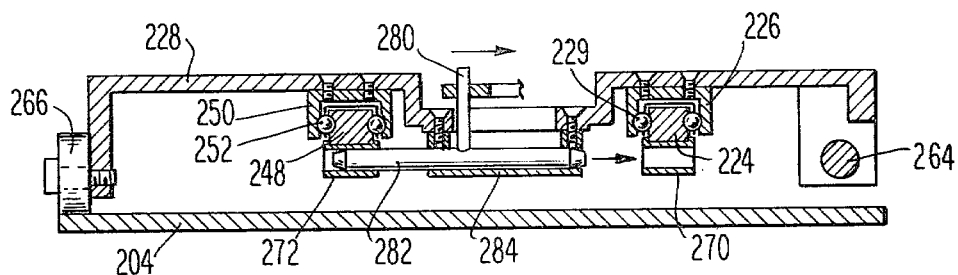

Thus, each inner race member 224 and 248 has an identical apertured member 270 and 272 mounted respectively thereto at an outer end thereof (FIGS. 9, 11 and 14). A selector lever 274 is pivotally mounted at 276 to top plate 228 and cooperates with a screw 280 which is threadedly received by a locking rod 282. Locking rod 282 is slidable within a guide block 284 which is mounted to top plate 228. Selector lever 274 is provided with a longitudinal slot 286 to permit screw 280 to ride within a guide slot 288 disposed longitudinally in guide block 284. Alternatively, guide slot 288 may be arcuated to obviate the need for longitudinal slot 286.

Selector lever 274 may be moved to cause locking rod 282 to engage apertured member 270 as shown in FIG. 12A if discontinuous radiographic images are desired, or, locking rod 282 may be moved into engagement with apertured member 272 (FIG. 12B) in order to obtain split or continuous images.

More specifically, when locking rod 282 is moved into position through selector lever 274 to provide split images, a limit switch 290, normally open, will close when selector lever 274 depresses limit switch arm 291. Now, upon actuation of chair shift motor 208 by conventional switch means aforediscussed, top plate 228 will shift to the left in response to chair shift motor 208 causing cam disc 212 to rotate 180° in a clockwise direction, although the invention would be equally operable if cam disc 212 were made to rotate in the other direction. Cam disc 212 rotates 180° each time chair shift motor 208 is separately actuated, since lobes 214, disposed 180° apart on cam disc 212, close and open the circuit to limit switch 216, as aforediscussed. Drive rod 218 (positioned as shown in FIG. 10) will thus be shifted in accordance therewith. When top plate 228 is thus shifted, outer races 250 and 226, both rigidly fixed to top plate 228, move along therewith. However, since cam follower 246, secured to inner race 248, engages groove 256 of plate cam 244, outer race 250 slides over inner race 248. Inner race 224, of course, moves with outer race 226. Y-motion travel is prevented by virtue of the X-direction alignment of the slide assemblies and slide bar arrangement 264. Thus, top plate 228, and chair L mounted thereabove, must shift to the left.

By merely actuating the chair shift motor again, top plate 228 will be returned to its original position by virtue of the interlock arrangement between top plate 228 with apertured member 270, rigidly connected to inner race 224. Absent such interlock, inner race 224 would merely slide rightwardly past stationary outer race 226 simultaneously with outer race 250 sliding to the right over inner race 248, with no resultant rightward shift of top plate 228, and chair L mounted thereupon.

Furthermore, it will be appreciated that the dentist, or operator, cannot return the chair to its original position by disengaging locking rod 282 from apertured member 270 after the chair has been shifted to the left since any attempt to do so will cause locking rod 282 to abut against outer race 250 to prevent such disengagement. In order to disengage locking rod 282 from apertured member 270, top plate 228 must be returned to its original starting position.

In the continuous mode of operation, locking rod 282 will engage apertured member 272, which simultaneously disengages the interlock between locking rod 282 and apertured member 270. Limit switch 292, normally open, will close when selector lever 274 is moved to depress microswitch arm 293. Actuation of motor 240 by conventional switch means will cause cam 244 to rotate in a counterclockwise direction, urging cam follower 246 to ride within groove 256. Since cam follower 246 is rigidly affixed to inner race 248, which is now interlocked with top plate 228 through locking rod 282, it is apparent that top plate 228 will travel to the left. Outer race 226, of course, simultaneously slides to the left over inner race 224 which is prevented from moving by virtue of the connection between drive rod 218 and inner race 224.

Cam 244 is limited in its extent of rotation in both directions by a pair of normally closed limit switches 296 and 298 (FIGS. 11 and 13). Reversible motor 240 is provided with an output shaft 300 which is threaded in order to accept nut 302 which is raised or lowered on shaft 300 as it rotates in one direction or the other. Nut 302 has a pin 304 extending laterally therefrom, which pin is permitted to ride in a vertical slot 306 provided in a support plate 308 which mounts limit switches 296 and 298. Nut 302 is restricted in its vertical movement by coupling 310 and hub bearing 312. Thus, upon rotation of threaded shaft 300, nut 302 will move vertically in one direction or the other. Pin 304 will contact one of limit switch arms 314 or 316, depending upon its direction of travel, to start or stop rotation of cam 244. Spacer 318 and motor adapter plate 319 complete the assembly.

To return top plate 228 to its initial or starting position, motor 240 will again be actuated after throwing a reversing switch, later described. Cam 244 will now rotate in the other direction to cause cam follower 246 to ride in groove 256. Since cam follower 246 is rigidly pinned to inner race 248 which is interlocked to top plate 228 through locking rod 282 and apertured member 272, top plate 228 through locking rod 282 will travel to the right as inner race 224 slides to the right with respect to inner race 224, held immobile by means of drive rod 218 connected thereto.

The chair transport mechanism would be equally operable if both slide assemblies were inverted such that the inner races were securely attached to underside portions of the top plate and the outer race were mounted in slidable relationship thereto.

Figure 15:
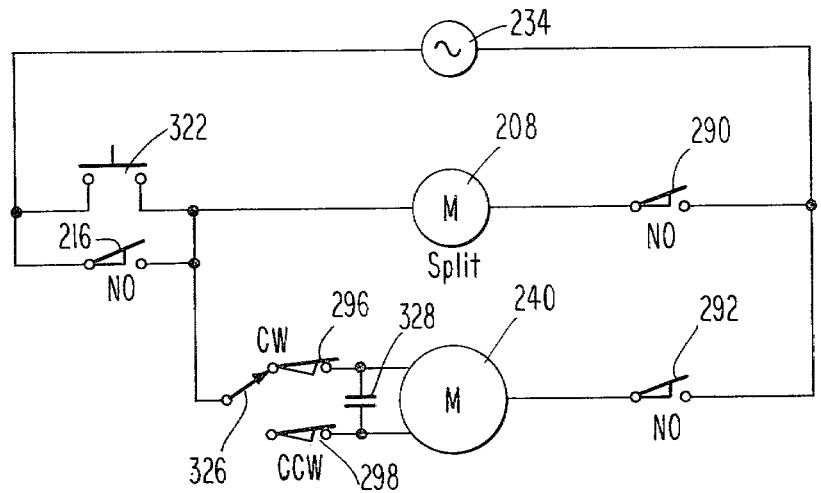
FIG. 15 is a schematic circuit diagram of electrical-mechanical safety interlock system of the chair transport mechanism.

Referring now to FIG. 15, when limit switch 290, normally open, is closed by the selector lever as aforedescribed, and push button switch 322 is caused to be depressed, or the circuit from A.C. power source 324 to chair shift motor 208 is completed, cam disc 212 starts to rotate such that one of the lobes 214 thereon immediately closes limit switch 216 to maintain the circuit closed until the other lobe of cam disc 212 returns limit switch 216 to its normally open position after 180° of rotation of the cam disc.

The continuous mode of operation cannot be initiated unless the chair is returned to its original or starting position, as described above.

In the continuous mode of operation, limit switch 292, normally open, is closed when the selector lever is moved into position for continuous image operation. Upon depressing push button switch 322, cam 244 will rotate in one direction or the other, depending upon the position of reversing switch 326, unless, of course, limit switch 296 or 298 prevents such rotation. Uninterrupted rotation of cam 244 requires that push botton switch 322 be continuously depressed, i.e., any release of switch 322 will open the circuit to motor 240. A capacitor 320 is interposed between motor 240 and limit switches 296 and 298.

We claim:

1. In a panoramic dental X-ray machine for providing continuous and discontinuous radiographic images of the dental arch area of a patient seated in a chair mounted on a mechanism affixed to a stationary platform of said X-ray machine, said X-ray machine having a column carrying
    (a) a tubehead containing an X-ray source, and (b) camera for holding film to be activated by said X-ray source,
    said machine including means to power said X-ray source and means for moving said film in said camera, and means for orbiting said column about said patient in a circular pattern, the improvement therewith wherein said mechanism comprises
    (A) means to shift said chair in an X-direction after said means to power said X-ray source have been rendered inoperative during a continuous orbit of said column about said patient when said X-ray source and said film are aligned with the spine of said patient to provide a discontinuous panoramic radiographic image of said dental arch area of said patient, and
    (B) other means for transporting said chair at a non-constant speed in an X-direction while said column continuously orbits the patient to provide a continuous panoramic radiographic image of said dental arch area of said patient, said mechanism comprising
        (a) a bottom plate rigidly supported by said stationary platform,
        (b) an upper plate disposed in spaced vertical relationship above said bottom plate, said upper plate being movable in an X-direction only,
        (c) means attached to each of said plates for permitting movement of said upper plate in said X-direction,
        (d) a cam mounted for rotation on an upper surface of said bottom plate, said cam having a non-radial groove disposed therein,
        (e) slide assembly means secured to an underportion of said upper plate,
        (f) a cam follower fixedly depending from said slide assembly means for cooperating with said groove of said cam for providing non-constant speed of said upper plate in said X-direction,
    said chair shift means urging said upper plate to move in said X-direction independently of movement of said upper plate by said other means.

2. X-ray machine as in claim 1 wherein said cam is a plate cam.

3. X-ray machine as in claim 1 wherein said chair shift means for urging said upper plate to move in said X-direction comprises,
    a motor mounted to said bottom plate, said motor having an output shaft,
    a double-lobed cam rotating in response to said output shaft,
    an arm fixedly mounted to said upper plate,
    a drive rod having one end off-centrally pivotally mounted to said double-lobed cam and its other end connected to one of said slide assembly means whereby rotation of said double-lobed cam causes said upper plate to move in an X-direction on said means attached to each of said plates for permitting movement of said upper plate in said X-direction.

4. X-ray machine as in claim 3 wherein said double-lobed cam is symmetrical having a pair of opposed lobes disposed 180° apart.

5. X-ray machine as in claim 2 wherein said slide assembly means includes a pair of similar slide assemblies, one of said slide assemblies comprising a first inner race slidable within a first outer race secured to an underportion of said upper plate, and the other of said slide assemblies comprising a second inner race slidable within a second outer race secured to another underportion of said upper plate,
    an apertured member secured to a forward portion of said first and second inner races,
    means pivotally mounted to said upper plate for separably engaging either of said inner races for interlocking said upper plate to one of said pair of slide assemblies.

6. X-ray machine as in claim 5 wherein rotation of said double-lobed cam causes said first inner race and first outer race to move in an X-direction with said upper plate, and said second outer race to slide over said second inner race when said cam follower is engaged within said groove of said plate cam.

7. X-ray machine as in claim 5 wherein rotation of said plate cam causes said second inner race and second outer race to move in an X-direction with said upper plate, and said first outer race to slide over said first inner race when a drive rod interconnecting said double-lobed cam and said first inner race remains motionless.

8. X-ray machine as in claim 6 when said pivotally mounted means engages said apertured member connected to said first inner race for providing return of said upper plate in an X-direction to its starting position.

9. X-ray machine as in claim 7 when said pivotally mounted means engages said apertured member connected to said second inner race for providing return of said upper plate in an X-direction to its starting position.

10. X-ray machine as in claim 8 wherein limit switch means cooperating with said pivotally mounted means prevents relative movement between said first inner race and first outer race.

11. X-ray machine as in claim 9 wherein limit switch means cooperating with said pivotally mounted means prevents relative movement between said second inner race and second outer race.

12. X-ray machine as in claim 11 wherein said plate cam is rotated by a plate cam motor through a plate cam shaft, said plate cam shaft being restricted in rotary motion by limiting means disposed below said bottom plate and operably associated therewith.

* * * * *